US010258765B2

(12) United States Patent
Kashimura et al.

(10) Patent No.: US 10,258,765 B2
(45) Date of Patent: Apr. 16, 2019

(54) CABLE AND MEDICAL HOLLOW TUBE (71) Applicant: Hitachi Metals, Ltd., Tokyo (JP)

(72) Inventors: Seiichi Kashimura, Hitachi (JP);
Takanobu Watanabe, Hitachi (JP);
Kimika Kudo, Kitaibaraki (JP);
Masamichi Kishi, Hitachinaka (JP)

(73) Assignee: HITACHI METALS, LTD., Tokyo (JP)

( * ) Notice: Subject to any disclaimer, the term of this patent is extended or adjusted under 35 U.S.C. 154(b) by 0 days.

(21) Appl. No.: 15/659,458

(22) Filed: Jul. 25, 2017

(65) Prior Publication Data
US 2018/0036509 A1 Feb. 8, 2018

(30) Foreign Application Priority Data

Aug. 2, 2016 (JP) .................. 2016-152104
Jun. 2, 2017 (JP) .................. 2017-109957

(51) Int. Cl.
| A61M 25/00 | (2006.01) |
|---|---|
| A61M 25/09 | (2006.01) |
| A61L 29/06 | (2006.01) |
| H01B 3/46 | (2006.01) |
| H01B 3/28 | (2006.01) |
| A61L 29/00 | (2006.01) |
| H01B 3/44 | (2006.01) |
| B05D 5/02 | (2006.01) |

(52) U.S. Cl.
CPC ......... *A61M 25/0045* (2013.01); *A61L 29/00* (2013.01); *A61M 25/005* (2013.01); *A61M 25/0068* (2013.01); *A61M 25/09* (2013.01); *H01B 3/28* (2013.01); *H01B 3/441* (2013.01); *A61M 2025/0048* (2013.01); *A61M 2025/09191* (2013.01); *C08L 2203/202* (2013.01)

(58) Field of Classification Search
CPC ......... A61L 29/085; A61M 2025/0046; A61M 2025/0048; C09D 183/04
USPC .................. 174/110 S; 604/264; 427/119
See application file for complete search history.

(56) References Cited

U.S. PATENT DOCUMENTS

| 3,434,869 A | * | 3/1969 | Davidson | ............... A61L 29/06 138/146 |
|---|---|---|---|---|
| 4,431,701 A | * | 2/1984 | Hamada | ................... C08K 3/36 174/110 S |
| 4,966,638 A | * | 10/1990 | Mudgett | ............... H01B 7/182 156/51 |
| 2007/0299402 A1 | | 12/2007 | Ishii et al. | |

FOREIGN PATENT DOCUMENTS

JP 2008-000287 A 1/2008

* cited by examiner

*Primary Examiner* — Fred M Teskin
(74) *Attorney, Agent, or Firm* — McGinn IP Law Group, PLLC.

(57) ABSTRACT

A cable includes a silicone rubber coating including microparticles and cavities as an outermost coating. A medial hollow tube includes a silicone rubber coating including microparticles and cavities as an outermost coating or an innermost coating. The microparticles may be at least one kind of microparticle selected from silicone resin microparticle, silicone rubber microparticle and silica microparticle. The microparticles may have hardness higher than a hardness of silicone rubber constituting the silicone rubber coating.

9 Claims, 6 Drawing Sheets

CABLE AND MEDICAL HOLLOW TUBE

The present application is based on Japanese patent application No. 2016-152104 filed on Aug. 2, 2016, and Japanese patent application No. 2017-109957 filed on Jun. 2, 2017, the entire contents of which are incorporated herein by reference.

BACKGROUND OF THE INVENTION

1. Field of the Invention

The present invention relates to a cable and a medical hollow tube.

2. Description of the Related Art

When silicone rubber is used as a material of an outermost layer of a cable such as medical probe cable, the silicone rubber has a large frictional resistance and a surface of the silicone rubber is sticky, which will deteriorate workability in operations such as operation of putting into and pulling out the cable from a packing envelope.

In medical devices such as catheters, the silicone rubber having a low impact on the physiological tissue is preferably used. There would be therefore a similar problem. Thus, it has been demanded to improve sliding property (See e.g., JP-A 2008-287).

SUMMARY OF THE INVENTION

Even though excellent sliding property can be achieved by e.g. giving irregularity (concavo-convex) processing on the surface of a silicone sheath outermost layer, it would be necessary to wipe off dirt, contamination and the like which is stuck on the surface of a cable for the application of repetitive use. There is however a problem as below. The surface irregularity will be scraped away in accordance with the increase in number of times of wiping-off, so that the sliding property will be deteriorated, namely, the frictional resistance will increase. As a result, the surface comes to be sticky.

Accordingly, it is an object of the present invention to provide a cable and a medical hollow tube with a wiping-off resistance which can maintain the excellent sliding property even though the number of times of wiping-off increases.

For achieving the above object, the present invention provides a cable and a medical hollow tube as described below.

[1] A cable comprising:
a silicone rubber coating including microparticles and cavities as an outermost coating.

[2] The cable according to [1], wherein the microparticles comprise at least one kind of microparticle selected from silicone resin microparticle, silicone rubber microparticle and silica microparticle.

[3] The cable according to [1] or [2], wherein the microparticles comprise a hardness higher than a hardness of silicone rubber constituting the silicone rubber coating.

[4] The cable according to any one of [1] to [3], wherein an average particle size of the microparticles is not less than 3 μm and not more than 20 μm.

[5] The cable according to any one of [1] to [4], wherein a content of the microparticles in the silicone rubber coating is not less than 10 mass % and not more than 50 mass %.

[6] The cable according to any one of [1] to [5], wherein a maximum length of each of the cavities is not less than 1 μm and not more than 15 μm.

[7] The cable according to any one of [1] to [6], wherein a thickness of the silicone rubber coating is not less than 3 μm and not more than 50 μm.

[8] The cable according to any one of [1] to [7], wherein a surface of the silicone rubber coating comprises an irregularity.

[9] The cable according to any one of [1] to [8], further comprising a sheath on which the silicone rubber coating is coated, the sheath comprising a compound including silicone rubber, or chloroprene rubber.

[10] A medial hollow tube, comprising:
a silicone rubber coating including microparticles and cavities as an outermost coating or an innermost coating.

(Points of the Invention)

According to the present invention, it is possible to provide a cable and a medical hollow tube with a wiping-off resistance which can maintain the excellent sliding property even though the number of times of wiping-off increases.

BRIEF DESCRIPTION OF THE DRAWINGS

Next, the present invention will be explained in conjunction with appended drawings, wherein:

FIGS. 2A to 2C are photographs showing a coating surface of the cable in the embodiment according to the present invention, wherein FIG. 2A is photographed at 200-fold magnification, FIG. 2B is photographed at 500-fold magnification, and FIG. 2C is photographed at 1,000-fold magnification;

FIGS. 4A and 4B are schematic cross-sectional views showing a film configuration of a cable concerning in comparative examples, wherein FIG. 4A shows a comparative example 1, and FIG. 4B shows a comparative example 2;

DETAILED DESCRIPTION OF THE EMBODIMENT (Cable)

A cable in the embodiment according to the present invention comprises a silicone rubber coating including microparticles and cavities as an outermost coating.

Figure 1:
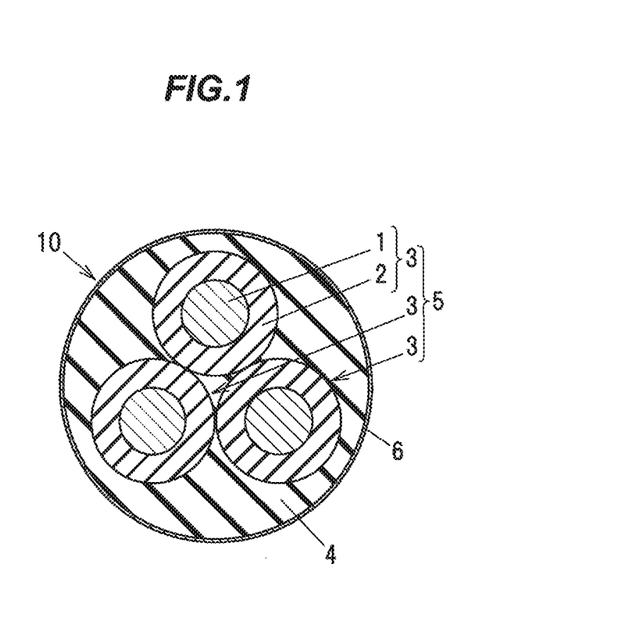
FIG. 1 is a transversal cross-sectional view showing an example of a cable in an embodiment according to the present invention.

The cable in the embodiment according to the present invention will be described below in more detail in conjunction with appended drawings. FIG. 1 is a transversal cross-sectional view showing an example of a cable in an embodiment according to the present invention.

FIG. 1 shows a cable 10 in the embodiment according to the present invention comprises a twisted core wire 5 comprising three twisted electric wires 3, a sheath 4 provided around an outer periphery of the twisted core wire 5 by extrusion coating, and a silicone rubber coating 6 formed around an outer periphery of the sheath 4. The electric wire 3 may be a single core wire or a stranded multi-core wire other than three cores.

The electric wire 3 comprises a conductor 1 comprising a general-purpose material, e.g., a pure copper or tinned copper (Sn-plated copper) and an insulator 2 coated around an outer periphery of the conductor 1. The material of the insulator 2 is not limited, as long as it can be used as an electrically insulating material for the electric wire. For example, the insulator 2 may comprise rubber materials such as polyethylene, polyvinyl chloride, Kapton (trademark), silicone rubber, and ethylene propylene (EPR), or fluorinated resins such as ETFE, FEP, PFA, and PTFE may be preferably used. The conductor 1 is not limited to a single wire, and may comprise a strand of a plurality of elementary wires. The electric wire 3 may comprise a coaxial wire or an optical fiber.

The material of the sheath 4 is not limited, as long as it can be used as sheath material. For example, silicone rubber, polyvinyl chloride, polyethylene, chlorinated polyethylene, chloroprene rubber may be preferably used. Particularly, the application value of the present invention is high when the sheath 4 comprises a material with low sliding property, i.e., materials with high frictional force or materials with high tackiness. For example, as typical materials, rubber compounds such as silicone rubber, chloroprene rubber having the tackiness (sticky property) with the coefficient of static friction $\mu$ of 0.7 or more when it is used as a base material of a sheet may be used. These materials may be used alone or a compound including two kinds or more thereof.

Generally-used compounding agents such as various crosslinking agents, crosslinking catalysts, antioxidants, plasticizers, lubricants, fillers, fire retardants, stabilizers, and coloring agents may be added to a compound to be used as the sheath material.

The sheath 4 may be formed by extrusion coating, and may be further treated with crosslinking processing, as necessary.

The sheath 4 may have a multi-layer configuration. In this case, the application value of the present invention is high when the outermost layer in the multi-layer configuration comprises the aforementioned materials.

The silicone rubber coating 6 is coated on the surface of the sheath 4 which is the outermost coating layer.

Figure 2A:
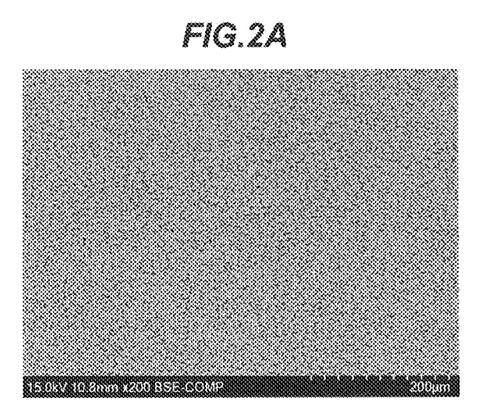
Figure 2B:
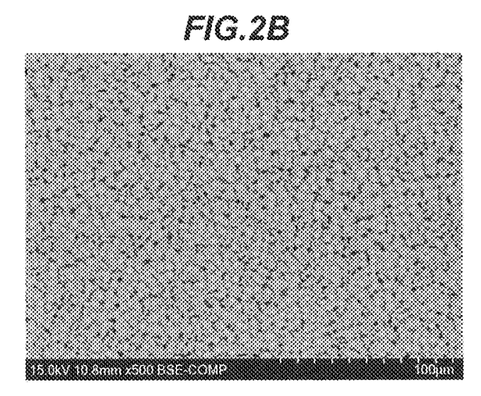
Figure 2C:
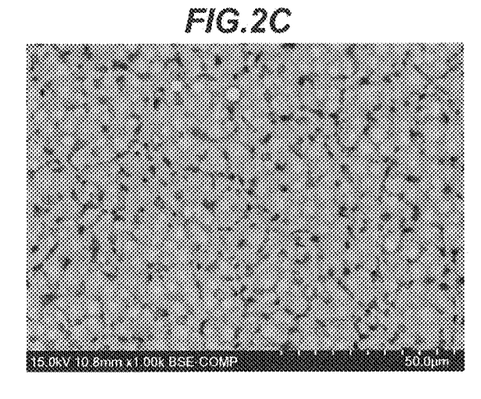
Figure 3:
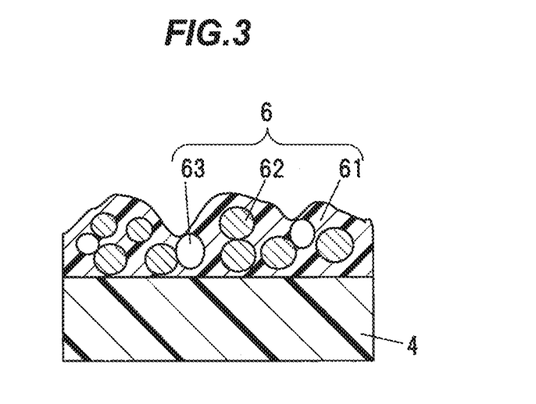
FIG. 3 is a schematic cross-sectional view showing a film configuration of the cable in the embodiment according to the present invention.

FIGS. 2A to 2C are photographs showing a coating surface of the cable in the embodiment according to the present invention, wherein FIG. 2A is photographed at 200-fold magnification, FIG. 2B is photographed at 500-fold magnification, and FIG. 2C is photographed at 1,000-fold magnification. FIG. 3 is a schematic cross-sectional view showing a film configuration of the cable in the embodiment according to the present invention.

The silicone rubber coating 6 includes a lot of microparticles 62 and a lot of cavities 63 in silicone rubber 61, as shown in FIGS. 2A to 2C, and the microparticles 62 and the cavities 63 are dispersed in the silicone rubber coating 6 entirely. In FIGS. 2A to 2C, white spherical parts correspond to the microparticles 62, and black spot parts correspond to the cavities 63. The microparticles 62 and the cavities 63 are dispersed uniformly in the entire part of the silicone rubber coating 6.

Also, it is preferable that the microparticles 62 are dispersed in a thickness direction of the silicone rubber coating 6 (cf. FIG. 3). Even though the microparticles 62 are scraped off during the wiping-off operation (or the neighboring silicone rubber 61 is scraped so that the microparticles 62 are removed), new microparticles 62 inside the silicone rubber 61 are exposed when the silicone rubber 61 is scraped. Therefore, it is possible to keep a small contact area with nonwoven fabrics for wiping-off, thereby maintaining a low coefficient of friction easily.

For the microparticles 62, various kinds of microparticles such as silicone resin microparticles, silicone rubber microparticles, silica microparticles, silver microparticles may be used, but it is preferable that microparticles have the hardness higher than the hardness of the silicone rubber 61 constructing the silicone rubber coating 6 (e.g. around 1.1 times or more in Shore hardness (Durometer A hardness)). The microparticles 62 preferably comprise at least one of microparticles selected from silicone resin microparticle, silicone rubber microparticle and silica microparticle, and more preferably silicone resin microparticle. The silicone rubber microparticle may be spherical powder comprising a spherical silicone rubber powder coated with silicone resin (so-called hybrid silicone powder).

The microparticle 62 is preferably spherical, and an average particle size of the microparticles 62 is preferably not less than 3 μm and not more than 20 μm, more preferably not less than 3.5 μm and not more than 15 μm, most preferably not less than 4 μm and not more than 10 μm.

Also, the content of the microparticles 62 in the silicone rubber coating 6 is preferably not less than 10 mass % and not more than 50 mass %, more preferably not less than 15 mass % and not more than 47 mass %, and most preferably not less than 20 mass % and not more than 45 mass %. When the content of the microparticles 62 in the silicone rubber coating 6 is less than 10 mass %, the abrasion resistance may be deteriorated. When the content of the microparticles 62 in the silicone rubber coating 6 exceeds 50 mass %, it becomes difficult for the microparticle 62 to adhere to the silicone rubber 61.

In the embodiment shown in FIGS. 2A to 2C, a silicone rubber surface modification coating material (brand name: X-93-1755-1, made by Shin-Etsu Chemical Co., Ltd.) is used for a coating for the silicone rubber 61. In the coating material, silicone resin microparticles (brand name: X-52-1621, made by Shin-Etsu Chemical Co., Ltd.) having the average particle size of 4.6 μm as the microparticles 62 are added and dispersed to provide a final coating liquid, and this final coating liquid is applied and dried to form the silicone rubber coating 6. The content of the silicone resin microparticles in the silicone rubber coating 6 is 45 mass %.

On the other hand, the maximum length of the cavity 63 is not less than 0.5 μm and not more than 20 μm, preferably not less than 1 μm and not more than 15 μm, and most preferably not less than 2 μm and not more than 10 μm.

Even if the cavities 63 are not numerous, the cavities 63 will contribute to the effect of the present invention, namely the improvement in the wiping-off resistance. It is however preferable that the number of the cavities 63 is within a range from −30% to +30% of the number of the microparticles 62. A plurality of cavities 63 may be coupled to each other.

In FIGS. 2A to 2C, the cavities 63 each of which has the maximum length of 3 to 10 nm are formed in the silicone rubber coating 6, and the number of the cavities 63 is within a range from about −20% to +20% of the number of the microparticles 62.

Figure 5:
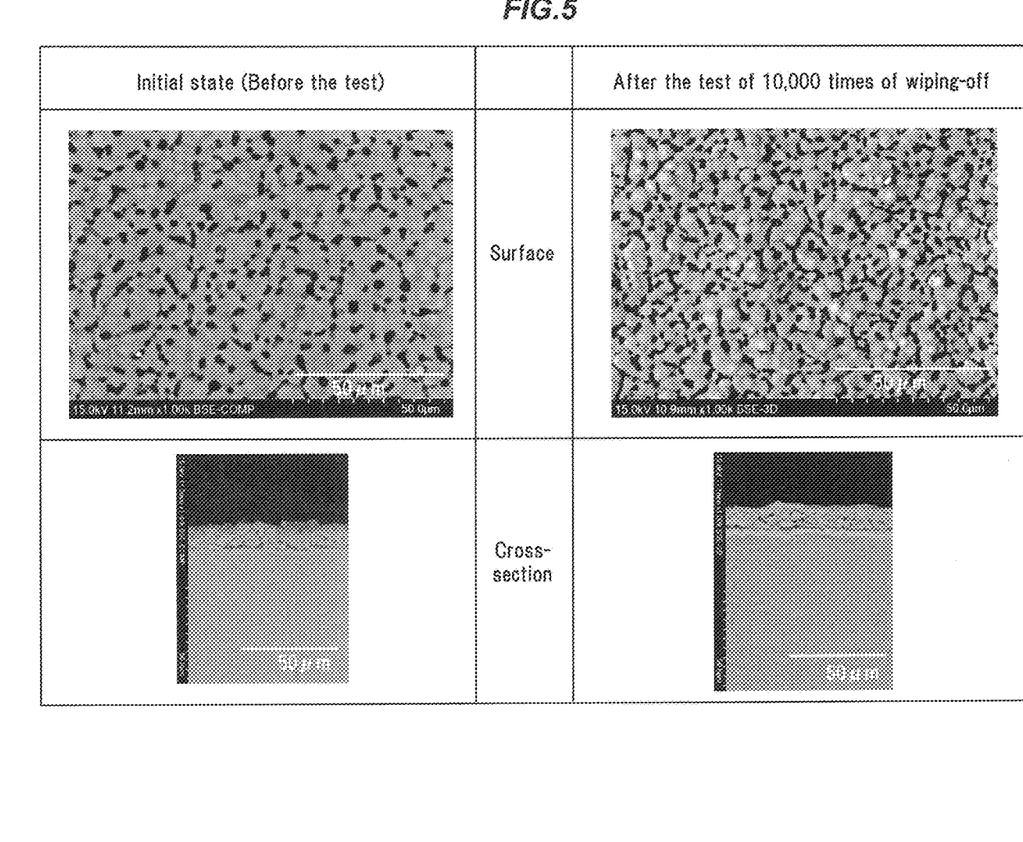
FIG. 5 is a photograph showing a coating surface and a cross-section of the cable in Example (before and after the wiping-off resistance test)

Also, it is preferable that the surface of the silicone rubber coating 6 has an irregularity as shown in cross-sectional views in FIG. 3 and FIG. 5. Thereby, it is possible to reduce a contact area with an object when the cable is moved, thereby further reduce the frictional force, and improve the sliding property. More specifically, a surface roughness is, for example, an arithmetical mean roughness (Ra) of preferably not less than 0.2 µm, more preferably not less than 0.4 µm, and most preferably not less than 0.6 µm. The upper limit of the arithmetical mean roughness (Ra) should not be limited, but preferably not less than 5 µm.

In FIG. 2, the surface roughness of the silicone rubber coating 6 is 0.5 µm of the arithmetical mean roughness (Ra). The measurement of the arithmetical mean roughness (Ra) was conducted by a super depth shape measurement microscope using a laser (Type: VK-8500 made by Keyence Corporation). The observation magnification was 500-fold magnification, the object distance was 298 µm, and the measurement area was adjusted in the height direction. The measurement was performed at the measurement pitch of 0.01 µm.

The thickness of the silicone rubber coating 6 is not limited, but preferably not less than 3 µm and not more than 50 µm, more preferably not less than 6 µm and not more than 30 µm, and most preferably not less than 7 µm and not more than 25 µm. In FIGS. 2A to 2C, the thickness of silicone rubber coating 6 was 15 µm.

The silicone rubber coating 6 may be formed by commonly-known methods, e.g., by dip coating method or spray coating method. As the coating solution, it is possible to use coating solution including microparticles 62 in the silicone rubber coating material including the volatile solvent to form the cavities 63. For example, as the volatile dilution solvent, toluene, n-heptane, benzene, ethylbenzene, o-xylene (1,2-dimethylbenzene), m-xylene (1,3-dimethylbenzene), p-xylene (1,4-dimethylbenzene) may be used. The number and size of the cavities 63 can be regulated by selecting a suitable volatile dilution solvent, and adjusting the content of the microparticles 62 and the content of the solvent. In the Examples shown in FIGS. 2A to 2C, silicone resin microparticles (brand name: X-52-1621, made by Shin-Etsu Chemical Co., Ltd.) having an average particle size of 4.6 µm was used as the microparticles 62, and a material including vinyl oxime silane, toluene, and n-heptane (brand name: X-93-1755-1, made by Shin-Etsu Chemical Co., Ltd.) was used as the coating material for the silicone rubber 61 including cavities. By using the solution comprising 10 parts by mass of the silicone resin microparticles to 100 parts by mass of the silicone rubber coating material, the silicone rubber coating 6 was formed by the dip coating method (pulling rate: 2 m/sec). Thereafter, the coating was dried for 60 minutes at temperature of 120 degrees Celsius. The proportion of the microparticles 62 in the coating 6 after the drying was 45%. This ratio was calculated based on non-volatile parts of 12% in the coating solution as shown in the description of the silicone rubber surface modification coating materials (X-93-1710, X-93-1755-1) in "Silicone News", Vol. 130, Shin-Etsu Chemical Co., Ltd.

More specifically, the proportion of the microparticles 62 in the coating 6 is calculated from (10 parts by mass <the mass of the microparticles 62>)/{(10 parts by mass <the mass of the microparticles 62>)+(100 parts by mass <the mass of the silicone rubber coating material>×0.12)}.

When the cavity diameter in the formed film is too small such as 0.1 µm, the diameter and the number of the cavities produced by volatilization can be adjusted by adding volatile dilute solvent such as toluene, n-heptane, benzene, ethylbenzene, o-xylene (1,2-dimethylbenzene), m-xylene (1,3-dimethylbenzene), p-xylene (1,4-dimethylbenzene) to the coating liquid. Also, the adjustment for increasing the cavity diameter can be performed appropriately by increasing the film thickness by increasing the pulling rate.

The cable 10 in the present embodiment may further comprise a separator, a braid, a shield tape made of a metal foil, or the like as necessity.

The cable in the embodiment according to the present invention is applicable to cables of various kinds of applications, and it is particularly suitable for the cables which are repeatedly used after wiping-off the dirt and have the problem of friction between the cables or the contacting object, e.g. medical cables (endoscope cable, probe cable, catheter connection cable, or the like) and cabtyre cables.

(Medical Hollow Tube)

The present invention is also applicable to the articles other than cables, that are repeatedly used after wiping off the dirt and have the problem of friction with the contacting object, and it is particularly suitable for the medical hollow tubes such as catheters. In other words, the medical hollow tube in the embodiment according to the present invention comprises a silicone rubber coating including microparticles and cavities as an outermost coating. The medical hollow tube in the embodiment according to the present invention may have a configuration similar to the well-known medical hollow tubes except that the medical hollow tube further comprises the aforementioned silicone rubber coating including the microparticles and the cavities as the outermost coating.

Also, the aforementioned silicone rubber coating including the microparticles and the cavities as the outermost coating may be used as an innermost coating (inner wall surface) of the medical hollow tube in the case where a medical instrument is inserted into the medical hollow tube such as catheters when used.

EXAMPLE

The present invention will be described in more detail below based on an example, but the present invention is not limited to this Example.

(Wiping-Off Resistance Evaluation of the Cable)

A cable having a configuration shown in FIG. 1 was prepared by a method as described below and the wiping-off resistance was evaluated.

The dimensions of respective parts of the cable (electric wire: three wires×22 mm$^2$) are as follows.

Conductor configuration (Outer diameter of the conductor/Number of elementary wires/Wire diameter): 7 mm/20/0.45 mm
Insulator thickness: 1.2 mm
Sheath thickness: 2.7 mm
Finished outer diameter: 26 mm The electric wire 3 was prepared as follows. Vulcanizing EPR (ethylene-propylene rubber) of each color (red, white, black) was provided around a conductor 1 to have a predetermined thickness by extrusion coating, and crosslinked by steam under pressure as an insulator 2, to provide an electric wire 3 of each color.

The three electric wires 3 of each color were twisted to provide a twisted core wire 5. Sheath material was provided around an outer periphery of the twisted core wire 5 by extrusion coating at a rate of 5 m/min with the use of an extruder, to provide a sheath 4. As the sheath material, silicone rubber was used.

After the sheath 4 was provided, a surface of the sheath 4 was cleaned. Thereafter, silicone rubber coating was formed around the surface of the sheath 4, to provide the cable in Example 1. More specifically, a silicone rubber coating 6 having a film thickness of 15 µm was formed by dip coating method at a pulling rate of 2 m/sec by using a solution including 10 parts by mass of silicone resin microparticles (brand name: X-52-1621, made by Shin-Etsu Chemical Co., Ltd.) having the average particle size of 4.6 μm with respect to 100 parts by mass of a silicone rubber coating material (brand name: X-93-1755-1, made by Shin-Etsu Chemical Co., Ltd.) including volatile solvents (n-heptane, toluene). The content of the silicone resin microparticles 62 in the silicone rubber coating 6 was 45 mass %. Further, cavities 63 having the maximum length of 3 to 10 μm were formed in the silicone rubber coating 6 and the number of the cavities 63 was within a range from about −20% to +20% of the number of the microparticles 62.

Then, cables in comparative examples 1 and 2 were prepared by changing the coating materials. The steps prior to the step of forming the coating on the surface of the sheath were similar to the steps in Example 1.

Figure 4A:
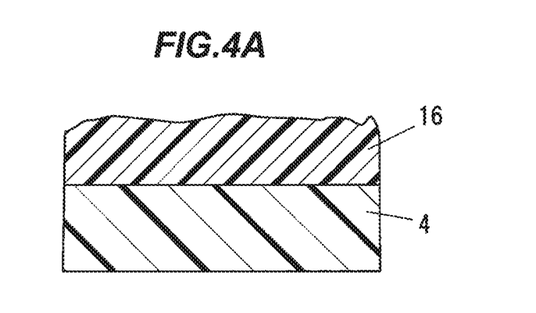

In the comparative example 1, a silicone resin coating 16 having a film thickness of 7 hm was formed by dip coating method at a pulling rate of 1.5 m/sec by using a silicone resin solution (brand name: X-93-1710, made by Shin-Etsu Chemical Co., Ltd.) including volatile solvents (n-heptane, toluene) (cf. FIG. 4A).

Figure 4B:
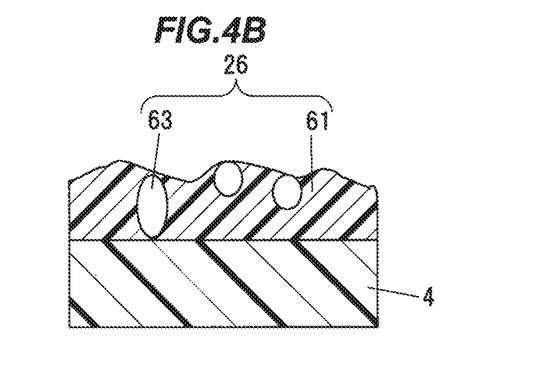

In the comparative example 2, a silicone rubber coating 26 having a film thickness of 7 μm was formed by dip coating method at a pulling rate of 2 m/sec by using a silicone rubber solution (brand name: X-93-1755-1, made by Shin-Etsu Chemical Co., Ltd.) (cf. FIG. 4B).

Evaluation samples were prepared by cutting pieces having a length of 15 cm, respectively, from the cables in Example 1 and the comparative examples 1 and 2. Thereafter, the wiping-off resistance test was carried out on the samples.

(Wiping-Off Resistance Testing Method)

Each testing sheet was preparing by making a cut in a longitudinal direction to a sheath portion of the cable, removing the components except the sheath, unrolling the sheath, and sticking the unrolled sheath on a flat plate to have dimensions of approximately 15 cm in length and 8 cm in width. One end of the testing sheet was grasped and a coating surface was swabbed with a 5 cm-square nonwoven fabric soaked with ethanol for sterilization for wiping-off. The nonwoven fabric was soaked with ethanol for sterilization for every ten times of wiping-off such that the nonwoven fabric would not dry. The nonwoven fabrics were exchanged for renewal for every 300 times of wiping-off. The wiping-off was performed repeatedly in one direction, and 10,000 times of wiping-off was conducted for Example 1 and the comparative example 2, and 5,000 times of wiping-off was conducted for the comparative example 1. A wiping force was measured by fixing the testing sheet on a measure and wiping off the coating surface while pressing thereon with the nonwoven fabric, and the force level was calculated based on the measured amount. This measurement was carried out every time before the wiping-off test so as to achieve the uniform force level. The specific wiping load was adjusted to be approximately 0.3 kg. The wiping-off was conducted at the rate of approximately 75 times/minute with a wiping distance of approximately 15 cm/time.

The coating surface was photographed (at 1,000-fold magnification) before and after the wiping-off resistance test. For Example 1, the cross-section was also photographed (at 1,000-fold magnification).

FIG. 5 is a photograph showing a coating surface and a cross-section of the cable in Example 1 (before and after the wiping-off resistance test).

Figure 6:
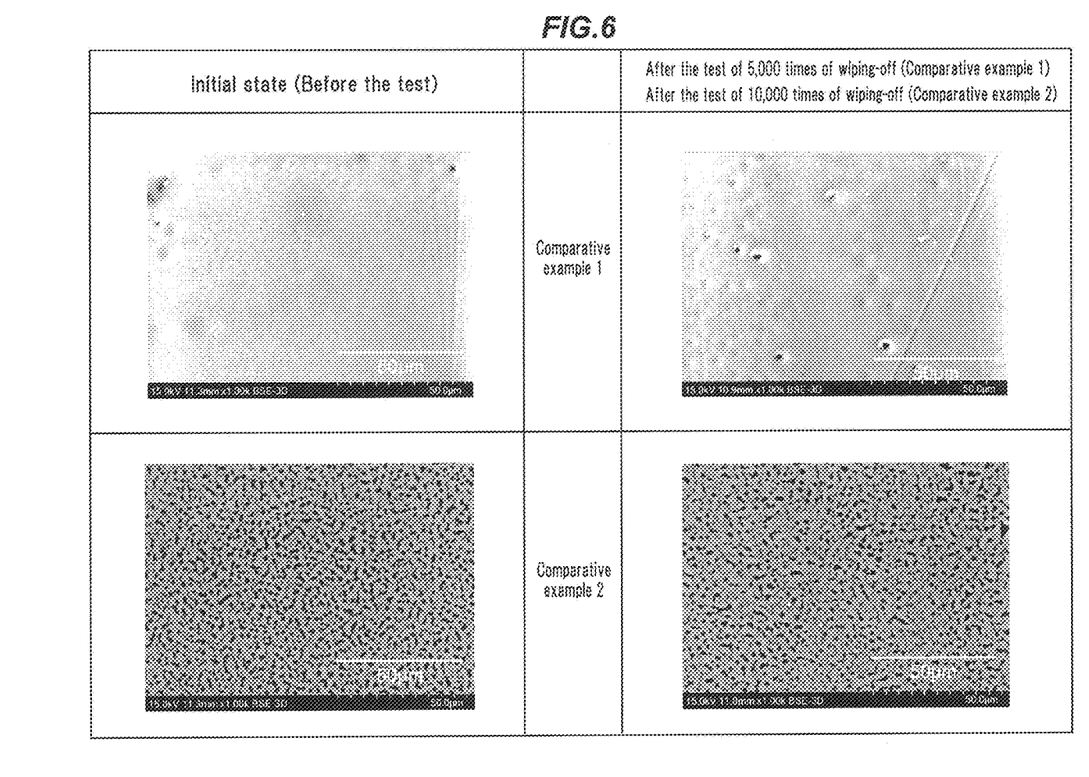
FIG. 6 is a photograph showing a coating surface of the cable in each of comparative examples (before and after the wiping-off resistance test)

FIG. 6 is a photograph showing a coating surface of the cable in each of comparative examples (before and after the wiping-off resistance test).

Also, the coefficient of static friction of the coating surface was measured before and after the wiping-off resistance test and during the wiping-off resistance test (500 times for the comparative example 1, and 5,000 times for Example 1 and comparative example 2).

The measurement of the coefficient of static friction was performed as follows. Similarly to the wiping-off resistance test, a sheet sample was prepared by processing the coated cable or the testing sheet after the wiping-off resistance test, sticking the sheet on a flat plate to have dimensions of approximately 10 cm in length and 2.5 cm in width (Sheet 1). Similarly, another sheet sample was prepared by processing the coated cable or the testing sheet after the wiping-off resistance test, cutting the sheet into 1.5 cm-square piece, and sticking the piece on a flat plate (Sheet 2). A pulling force (frictional force) F was measured by pushing the sheet 2 downwardly to contact with the sheet 1 such that a coating surface or wiped-off surface of the sheet 2 faces to a coating surface or wiped-off surface of the sheet 1, and pulling the flat plate of the sheet 2 horizontally in a push-pull gauge while applying load W of 2N on the flat plate of the sheet 2. The coefficient of static friction $\mu$ was calculated from $F=\mu W$.

Figure 7:
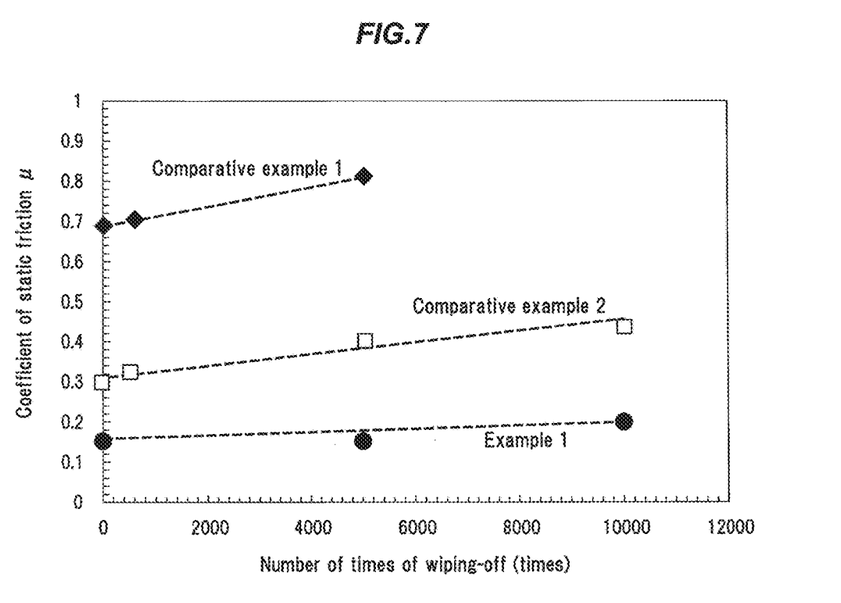
FIG. 7 shows graphs indicating the coefficients of static friction in the wiping-off resistance test in Example and the comparative examples.

FIG. 7 shows graphs indicating the coefficients of static friction in the wiping-off resistance test in the Example and the comparative examples.

As clearly understood from FIG. 7, in Example 1, the surface of the cable comprising the silicone rubber coating 6 including the microparticles and the cavities as the outermost coating has a small coefficient of static friction before and after the wiping-off resistance test (0.16 before the test, and 0.18 after 10,000 times of wiping-off). Namely, the cable with a sufficient wiping-off resistance, which can maintain the excellent sliding property even though the number of times of wiping-off increases (namely, less sticky), was provided. On the other hand, in the cables of the comparative examples 1 and 2, the coefficients of static friction were higher than that of the cable in Example 1, and the coefficients of static friction were greatly increased after the wiping-off resistance test (0.7 before the test and 0.82 after wiping-off of 5,000 times for the comparative example 1) (0.3 before the test and 0.43 after wiping-off of 10,000 times for the comparative example 2).

The silicone rubber coating 6 has the cavities 63, and has a sponge-like configuration. Therefore, it is assumed that the silicone rubber coating 6 easily transforms due to the stress applied at the time of the wiping-off resistance test and functions to dissipate this stress so that the wiping-off resistance of the surface of the cable in Example 1 was improved. Thus, in Example 1, the cable comprising the silicone rubber coating 6 including the microparticles and the cavities as the outermost coating does not exhibit the sticky feeling on the surface at an initial state, after wiping-off of 5,000 times, and after wiping-off of 10,000 times, and the coefficient of static friction of the surface was not more than 0.3, preferably not more than 0.25, and most preferably not more than 0.20.

Table 1 shows the arithmetical mean roughness (Ra) measured before and after the wiping-off resistance test. The arithmetical mean roughness (Ra) was measured with the user of a laser microscope system (VK-8500: made by Keyence Corporation).

TABLE 1

|  | Example 1 | | Comparative Example 1 | | Comparative Example 2 | |
|---|---|---|---|---|---|---|
| Unit: μm | Before the test | After the test (10,000 times) | Before the test | After the test (10,000 times) | Before the test | After the test (5,000 times) |
| Arithmetical mean roughness | 0.74 | 0.60 | 0.2 | 0.1 | 0.45 | 0.28 |

As clearly understood from Table 1, the surface of the cable comprising the silicone rubber coating 6 including the microparticles and the cavities in Example 1 has the arithmetical mean roughness (Ra) which was greater than the those of the surfaces of the cables in the comparative examples 1 and 2, and the decrease in the arithmetical mean roughness (Ra) remained about 20%.

In addition, the cables in Example 1 and the comparative example 2 had excellent flexibility, while cracks occurred in the cable in the comparative example 1 when being bent (R=5 mm), namely the flexibility was not enough.

It should be noted that the present invention is not limited to the above embodiment and Example, and the present invention can be appropriately modified and implemented without departing from the gist thereof.

For example, an adhesion reinforcing layer comprising a primer or silane coupling agent to increase the adhesiveness between the sheath and the silicone rubber coating may be provided on the surface of the sheath. Further, a surface modified layer may be provided on the surface of the sheath to increase the adhesiveness between the sheath and the silicone rubber coating. The surface modified layer may be formed by flame treatment for exposing the surface of the sheath to the flames for a short time, plasma treatment for colliding ionized or radicalized gas on the surface of the sheath, corona treatment for exposing the surface of the sheath to the atmospheric components ionized by the electrical discharge in the atmosphere, or the like. Furthermore, the silicone rubber coating may be formed after providing the adhesion reinforcing layer on the surface modified layer.

Also, when a probe cable is manufactured by attaching a probe main body including a cable bush to one end of the cable, an adhesive may be applied on the silicone rubber coating located at the end, and the cable bush may be fixed via this adhesive layer. In addition, the cable bush may be adhered and fixed by using the adhesion reinforcing layer and the adhesive layer together or the surface modified layer and the adhesive layer together. The adhesion reinforcing layer and the surface modified layer may be formed only at locations to which the cable bush should be fixed or over an entire length of the sheath.

Alternatively, the cable bush may be adhered and fixed to the sheath directly by the adhesive without providing any silicone rubber coating on the location to which the cable bush is attached, by previously masking or removing the silicone rubber coating, and the like. Also, the cable bush may be adhered and fixed to the sheath by the adhesive applied on the surface modified layer formed o the location where no silicone rubber coating is provided.

(Tensile Shear Strength Testing Method)

Two silicone rubber sheets each of which has dimensions of 25 mm in width and 15 mm in length were prepared. On one of the two silicone rubber sheets, a liquid silicone rubber based adhesive was applied in a region of 25 mm in width and 10 mm in length. The two silicone rubber sheets were adhered and fixed to each other via this adhesive layer to provide a tensile shear strength test sample of test example 1.

The tensile shear strength test sample of test example 2 was prepared by adding the step of forming a silicone rubber coating to the preparation process of the tensile shear strength test sample of test example 1. The other steps of test example 2 are the same as those for test example 1. More specifically, the silicone rubber coating was formed on the entire surface of the one silicone rubber sheet. The two silicone rubber sheets were adhered and fixed to each other via the adhesive layer made of the liquid silicone rubber-based adhesive formed on the silicone rubber coating.

The tensile shear strength test sample of test example 3 was prepared by adding the step of forming a surface modified layer and the step of forming a silicone rubber coating to the preparation process of the tensile shear strength test sample of test example 1. The other steps of test example 3 are the same as those for test example 1. More specifically, the surface modified layer was formed on the one silicone rubber sheet by flame treatment and the silicone rubber coating was formed on the entire surface of the surface modified layer of the one silicone rubber sheet. The two silicone rubber sheets were adhered and fixed to each other via the adhesive layer made of the liquid silicone rubber-based adhesive formed on the silicone rubber coating.

The silicone rubber coating in test examples 2 and 3 were formed under the same condition as that in test example 1.

The tensile shear strength (the maximum load when a sample is broken) was evaluated by pulling the tensile shear strength test samples 1 to 3 at a pulling rate of 500 mm/min in a direction parallel to a bonded surface.

TABLE 2

|  | Test example 1 | Test example 2 | Test example 3 |
|---|---|---|---|
| Silicone rubber coating | Absent | Present | Present |
| Surface modified layer | Absent | Absent | Present |
| Tensile shear strength (N) | 109 | 50 | 83 |

As clearly understood from test examples 1 and 2, when the silicone rubber sheets are stuck to each other, the tensile shear strength of 100N or more can be obtained, while the tensile shear strength was 50N in the case of providing the silicone rubber coating as an intervention. It is assumed that this is caused by a low bonding strength between the silicone rubber coating and the silicone rubber sheet, or between the silicone rubber coating and the adhesive layer, alternatively by high tensile shear strength of the coating per se.

In contrast, as clearly understood from test examples 2 and 3, the tensile shear strength of 80N or more can be obtained by forming the surface modified layer between the silicone rubber coating and the silicone rubber sheet, thereby increasing the adhesiveness between the silicone rubber coating and the silicone rubber sheet. Further, the tensile shear strength can be further increased by forming the adhesion reinforcing layer or the surface modified layer between the adhesive layer and the silicone rubber coating or the high tensile strength film.

What is claimed is:
1. A cable comprising:
  a silicone rubber coating including microparticles and cavities as an outermost coating.

2. The cable according to claim 1, wherein the microparticles comprise at least one kind of microparticle selected from silicone resin microparticle, silicone rubber microparticle and silica microparticle.

3. The cable according to claim 1, wherein the microparticles comprise a hardness higher than a hardness of silicone rubber constituting the silicone rubber coating.

4. The cable according to claim 1, wherein an average particle size of the microparticles is not less than 3 μm and not more than 20 μm.

5. The cable according to claim 1, wherein a content of the microparticles in the silicone rubber coating is not less than 10 mass % and not more than 50 mass %.

6. The cable according to claim 1, wherein a maximum length of each of the cavities is not less than 1 μm and not more than 15 μm.

7. The cable according to claim 1, wherein a thickness of the silicone rubber coating is not Less than 3 μm and not more than 50 μm.

8. The cable according to claim 1, wherein a surface of the silicone rubber coating comprises an irregularity.

9. The cable according to claim 1, further comprising a sheath on which the silicone rubber coating is coated, the sheath comprising a compound including silicone rubber, or chloroprene rubber.

* * * * *